United States Patent [19]
Monia et al.

[11] Patent Number: 5,919,773
[45] Date of Patent: *Jul. 6, 1999

[54] ANTISENSE OLIGONUCLEOTIDE MODULATION OF RAF GENE EXPRESSION

[75] Inventors: Brett P. Monia, Carlsbad, Calif.; Pierre Martin, Rheinfelden; Karl-Heinz Altmann, Reinach, both of Switzerland

[73] Assignees: Isis Pharmaceuticals, Inc., Carlsbad, Calif.; Ciba-Geigy, Ltd., Basel, Switzerland

[*] Notice: This patent is subject to a terminal disclaimer.

[21] Appl. No.: 08/977,424

[22] Filed: Nov. 24, 1997

Related U.S. Application Data

[60] Division of application No. 08/463,912, Jun. 5, 1995, Pat. No. 5,744,362, which is a continuation-in-part of application No. 08/250,856, May 31, 1994, Pat. No. 5,563,255.

[51] Int. Cl.$^6$ .............................. A61K 48/00; C12N 5/08
[52] U.S. Cl. .............................................. 514/44; 435/375
[58] Field of Search ................................ 435/6, 375, 377; 514/44; 536/24.31, 24.5

[56] References Cited

U.S. PATENT DOCUMENTS

| | | | |
|---|---|---|---|
| 4,806,463 | 2/1989 | Goodchild et al. | 435/5 |
| 5,004,810 | 4/1991 | Draper et al. | 536/24.5 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,166,195 | 11/1992 | Ecker et al. | 514/44 |
| 5,194,428 | 3/1993 | Agrawal et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,656,612 | 8/1997 | Monia | 514/44 |
| 5,744,362 | 4/1998 | Monia et al. | 435/375 |

FOREIGN PATENT DOCUMENTS

| | | |
|---|---|---|
| WO93/04170 | 3/1993 | WIPO . |
| WO93/06248 | 4/1993 | WIPO . |
| WO94/15645 | 7/1994 | WIPO . |

OTHER PUBLICATIONS

Antisense '97: A roundtable on the state of the industry. Nature Biotechnology 15: 519–524, Jun. 1997.

Gewirtz et al. Facilitating oligonucleotide delivery: Helping antisense deliver on its promise. Proc. Natl. Acad. Sci. USA 93, pp. 3161–3163, Apr. 1996.

Gura. Antisense has growing pains. Science 270: 575–577, Oct. 1995.

Rojanasakul. Antisense oligonucleotide therapeutics: Drug delivery and targeting. Adv. Drug Deliv. Rev. 18: 115–131, 1996.

Bennett et al., *J. Clin. Invest.* 1994, 93, 820–828.

*BioWorld Today*, Apr. 29, 1994, p. 3. It is thus.

Isobe et al., *Circulation* 1991, 84, 1246–1255.

Kingston, R.E., in *Current Protocols in Molecular Biology*, (F.M. Ausubel, R. Brent, R.E. Kingston, D.D. Moore, J.A. Smith, J.G. Seidman and K. Strahl, eds.), John Wiley and Sons, NY, 1993.

Martin, P., *Helv. Chim. Acta* 1995, 78, 486–504.

Rapp et al., *The Oncogene Handbook*, E.P. Reddy, A.M Skalka and T. Curran, eds., Elsevier Science Publishers, New York, 1988, pp. 213–253.

Riedel et al., *Eur. J. Immunol.* 1993, 23, 3146–3150.

Sambrook et al., *Molecular Cloning. A Laboratory Manual*, Cold Spring Harbor Laboratory Press, 1989, vol. 2, p. 10.59.

Sambrook et al., *Molecular Cloning. A Laboratory Manual*, Cold Spring Harbor Laboratory Press, 1989, vol. 2, pp. 11.31–11.32.

Tornkvist et al., *J. Biol. Chem.* 1994, 269, 13919–13921.

*Primary Examiner*—George C. Elliott
*Assistant Examiner*—Thomas G. Larson
*Attorney, Agent, or Firm*—Law Offices of Jane Massey Licata

[57] ABSTRACT

Oligonucleotides are provided which are targeted to nucleic acids encoding human c-raf and capable of inhibiting raf expression. The oligonucleotides contain a methoxyethoxy (2'—O—$CH_2CH_2OCH_3$) modification at the 2' position of at least one nucleotide. Methods of inhibiting the expression of human raf using oligonucleotides of the invention are also provided. The present invention further comprises methods of inhibiting hyperproliferation of cells and methods of treating abnormal proliferative conditions which employ oligonucleotides of the invention.

4 Claims, 4 Drawing Sheets

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 20
      (B) TYPE: Nucleic Acid
      (C) STRANDEDNESS: Single
      (D) TOPOLOGY: Linear    (iv) ANTI-SENSE: Yes    (xi) SEQUENCE DESCRIPTION: SEQ ID NO: 1:

TCCCGCCTGT GACATGCATT                                 20

ANTISENSE OLIGONUCLEOTIDE MODULATION OF RAF GENE EXPRESSION

This is a division of application Ser. No. 08/463,912, filed Jun. 5, 1995, now U.S. Pat. No. 5,744,362, which is a continuation-in-part of U.S. patent application Ser. No. 08/250,856, filed May 31, 1994, now U.S. Pat. No. 5,563,255.

FIELD OF THE INVENTION

This invention relates to compositions and methods for modulating expression of the raf gene, a naturally present cellular gene which has been implicated in abnormal cell proliferation and tumor formation. This invention is also directed to methods for inhibiting hyperproliferation of cells; these methods can be used diagnostically or therapeutically. Furthermore, this invention is directed to treatment of conditions associated with expression of the raf gene.

BACKGROUND OF THE INVENTION

Alterations in the cellular genes which directly or indirectly control cell growth and differentiation are considered to be the main cause of cancer. The raf gene family includes three highly conserved genes termed A-, B- and c-raf (also called raf-1) . Raf genes encode protein kinases that are thought to play important regulatory roles in signal transduction processes that regulate cell proliferation. Expression of the c-raf protein is believed to play a role in abnormal cell proliferation since it has been reported that 60% of all lung carcinoma cell lines express unusually high levels of c-raf mRNA and protein. Rapp et al., The Oncogene Handbook, E. P. Reddy, A. M Skalka and T. Curran, eds., Elsevier Science Publishers, New York, 1988, pp. 213–253.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases.

As examples, U.S. Pat. No. 5,135,917, issued Aug. 4, 1992, provides antisense oligonucleotides that inhibit human interleukin-1 receptor expression. U.S. Pat. No. 5,098,890, issued Mar. 24, 1992 in the name of Gewirtz et al., is directed to antisense oligonucleotides complementary to the c-myb oncogene and antisense oligonucleotide therapies for certain cancerous conditions. U.S. Pat. No. 5,087,617, issued Feb. 11, 1992, provides methods for treating cancer patients with antisense oligonucleotides. U.S. Pat. No. 5,166,195 issued Nov. 24, 1992, provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. U.S. Pat. No. 5,286,717 (Cohen et al.), issued Feb. 15, 1994, is directed to a mixed linkage oligonucleotide phosphorothioates complementary to an oncogene; U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely administered to humans and clinical trials of several antisense oligonucleotide drugs, targeted both to viral and cellular gene products, are presently underway. The phosphorothioate oligonucleotide, ISIS 2922, has been shown to be effective against cytomegalovirus retinitis in AIDS patients. BioWorld Today, Apr. 29, 1994, p. 3. It is thus established that oligonucleotides can be useful therapeutic instrumentalities and can be configured to be useful in treatment regimes for treatment of cells and animal subjects, especially humans.

Antisense oligonucleotide inhibition of gene expression has proven to be a useful tool in understanding the roles of raf genes. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., Eur. J. Immunol. 1993, 23, 3146–3150. Rapp et al. have disclosed expression vectors containing a raf gene in an antisense orientation downstream of a promoter, and methods of inhibiting raf expression by expressing an antisense Raf gene or a mutated Raf gene in a cell. Wo application 93/04170. An antisense oligodeoxyribonucleotide complementary to codons 1–6 of murine c-Raf has been used to abolish insulin stimulation of DNA synthesis in the rat hepatoma cell line H4IIE. Tornkvist et al., J. Biol. Chem. 1994, 269, 13919–13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation.

Denner et al. disclose antisense polynucleotides hybridizing to the gene for raf, and processes using them. Wo 94/15645. Oligonucleotides hybridizing to human and rat raf sequences are disclosed.

Iversen et al. disclose heterotypic antisense oligonucleotides complementary to raf which are able to kill ras-activated cancer cells, and methods of killing raf-activated cancer cells. Numerous oligonucleotide sequences are disclosed, none of which are actually antisense oligonucleotide sequences.

There remains a long-felt need for improved compositions and methods for inhibiting raf gene expression.

SUMMARY OF THE INVENTION

The present invention provides oligonucleotides which are targeted to nucleic acids encoding human raf and are capable of inhibiting raf expression. The oligonucleotides contain a methoxyethoxy (2'—O—$CH_2CH_2OCH_3$) modification at the 2' position of at least one nucleotide. These oligonucleotides are believed to be useful both diagnostically and therapeutically, and are believed to be particularly useful in the methods of the present invention.

The present invention also comprises methods of inhibiting the expression of human raf, particularly the abnormal expression of raf, using the oligonucleotides of the invention. These methods are believed to be useful both therapeutically and diagnostically as a consequence of the association between raf expression and hyperproliferation. These methods are also useful as tools, for example for detecting and determining the role of raf expression in various cell functions and physiological processes and conditions and for diagnosing conditions associated with raf expression.

The present invention also comprises methods of inhibiting hyperproliferation of cells using oligonucleotides of the invention. These methods are believed to be useful, for example in diagnosing raf-associated cell hyperproliferation. Methods of treating abnormal proliferative conditions are also provided. These methods employ the oligonucleotides of the invention. These methods are believed to be useful both therapeutically and as clinical research and diagnostic tools.

DETAILED DESCRIPTION OF THE INVENTION

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. The raf genes are members of a gene family which encode related proteins termed A-, B- and c-raf. Raf genes code for highly conserved serine-threonine-specific protein kinases. These enzymes are differentially expressed; c-raf, the most thoroughly characterized, is expressed in all organs and in all cell lines that have been examined. A- and B-raf are expressed in urogenital and brain tissues, respectively. c-raf protein kinase activity and subcellular distribution are regulated by mitogens via phosphorylation. Various growth factors, including epidermal growth factor, acidic fibroblast growth factor, platelet-derived growth factor, insulin, granulocyte-macrophage colony-stimulating factor, interleukin-2, interleukin-3 and erythropoietin, have been shown to induce phosphorylation of c-raf. Thus, c-raf is believed to play a fundamental role in the normal cellular signal transduction pathway, coupling a multitude of growth factors to their net effect, cellular proliferation.

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following angioplasty. The cellular signalling pathway of which raf is a part has also been implicated in inflammatory disorders characterized by T-cell proliferation (T-cell activation and growth), such as tissue graft rejection, endotoxin shock, and glomerular nephritis, for example.

It has now been found that elimination or reduction of raf gene expression can halt or reverse abnormal cell proliferation. This has been found even when levels of raf expression are not abnormally high. There is a great desire to provide compositions of matter which can modulate the expression of the raf gene. It is greatly desired to provide methods of detection of the raf gene in cells, tissues and animals. It is also desired to provide methods of diagnosis and treatment of abnormal proliferative conditions associated with abnormal raf gene expression. In addition, kits and reagents for detection and study of the raf gene are desired. "Abnormal" raf gene expression is defined herein as abnormally high levels of expression of the raf protein, or any level of raf expression in an abnormal proliferative condition or state.

The present invention employs oligonucleotides targeted to nucleic acids encoding raf. This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence hose function is to be modulated. This may be, as examples, a cellular gene (or mRNA made from the gene) whose expression is associated with a particular disease state, or a foreign nucleic acid from an infectious agent. In the present invention, the target is a nucleic acid encoding raf; in other words, the raf gene or mRNA expressed from the raf gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of raf gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to nontarget sequences under conditions in which specific binding is desired, i.e., under physiological conditions in the case of in vivo assays or therapeutic treatment or, in the case of in vitro assays, under conditions in which the assays are conducted.

In the present invention, oligonucleotides are provided which are targeted to MRNA encoding c-raf. In accordance with this invention, persons of ordinary skill in the art will understand that mRNA includes not only the coding region which carries the information to encode a protein using the three letter genetic code, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated which are targeted wholly or in part to these associated ribonucleotides as well as to the coding ribonucleotides. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with raf protein expression.

The present invention provides oligonucleotides for modulation of raf gene expression. Such oligonucleotides are targeted to nucleic acids encoding c-raf.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Modifications may be on one or more bases, sugars, or backbone linkages, or combinations of these; such modifications are well known in the art. Modified or substituted oligonucleotides are often preferred over native forms because of properties such as, for example, enhanced cellular uptake and increased stability in the presence of nucleases.

The oligonucleotides may be chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one embodiment, a chimeric oligonucleotide comprises at least one region modified to increase target binding affinity, and, usually, a region that acts as a substrate for RNAse H. Affinity of an oligonucleotide for its target (in this case a nucleic acid encoding raf) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of raf gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotide modifications which enhance target binding affinity are also, independently, able to enhance nuclease resistance.

The oligonucleotides of the present invention contain a methoxyethoxy (2'—O—$CH_2CH_2OCH_3$) modification at the 2' position of at least one nucleotide. This modification has been shown to increase both affinity of the oligo nucleotide for its target and nuclease resistance of the oligonucleotide. Oligonucleotides in accordance with this invention are preferably from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Martin, P., Helv. Chim. Acta 1995, 78,486–504. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

It has now been found that certain oligonucleotides targeted to portions of the c-raf mRNA are particularly useful for inhibiting raf expression and for interfering with cell hyperproliferation. Methods for inhibiting c-raf expression using antisense oligonucleotides are, likewise, useful for interfering with cell hyperproliferation. In the methods of the invention, tissues or cells are contacted with oligonucleotides. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of inhibiting hyperproliferation of cells and methods of treating abnormal proliferative conditions are provided. The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions of this invention may be administered in a number of ways depending upon whether local or systemic treatment is desired, and upon the area to be treated. Administration may be topical (including ophthalmic, vaginal, rectal, intranasal), oral, or parenteral, for example by intravenous drip, intravenous injection or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is Lipofectin (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on $EC_{50}$'s in in vitro and in vivo animal studies. For example, given the molecular weight of compound (derived from oligonucleotide sequence and chemical structure) and an effective dose such as an $IC_{50}$, for example (derived experimentally), a dose in mg/kg is routinely calculated.

The present invention is also suitable for diagnosing abnormal proliferative states in tissue or other samples from patients suspected of having a hyperproliferative disease such as cancer, psoriasis or blood vessel restenosis or atherosclerosis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish raf-associated tumors from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of raf expression. For example, radiolabeled oligonucleotides can be prepared by $^{32}p$ labeling at the 5' end with polynucleotide kinase. Sambrook et al., Molecular Cloning. A Laboratory Manual, Cold Spring Harbor Laboratory Press, 1989, Volume 2, p. 10.59. Radiolabeled oligonucleotides are then contacted with tissue or cell samples suspected of raf expression and the sample is washed to remove unbound oligonucleotide. Radioactivity remaining in the sample indicates bound oligonucleotide (which in turn indicates the presence of raf) and can be quantitated using a scintillation counter or other routine means. Radiolabeled oligo can also be used to perform autoradiography of tissues to determine the localization, distribution and quantitation of raf expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing raf. Quantitation of the silver grains permits raf expression to be detected.

Analogous assays for fluorescent detection of raf expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling VA. See 1993 Catalog of Products for DNA Research, Glen Research, Sterling Va., p. 21).

Each of these assay formats is known in the art. One of skill could easily adapt these known assays for detection of raf expression in accordance with the teachings of the invention providing a novel and useful means to detect raf expression.

Inhibition of c-raf expression by an oligonucleotide having SEQ ID NO: 1

Phosphorothioate deoxyoligonucleotides targeted to human c-raf were designed using the Genbank c-raf sequence HUMRAFR (Genbank listing x03484), synthesized and tested for inhibition of c-raf mRNA expression in T24 bladder carcinoma cells using a Northern blot assay. Oligonucleotide ISIS 5132 (TCCCGCCTGTGACATGCATT; SEQ ID NO: 1), targeted to the 3'UTR of c-raf, showed greater than 90% inhibition.

Two oligonucleotides having SEQ ID NO: 1 and an 8-nucleotide deoxynucleotide central region flanked on each side by 6 nucleotides having the 2'—O—$CH_2CH_2OCH_3$ modification were synthesized. These compounds differ in that one of them, ISIS 10755 (also known as CIBA 1440) has a uniform phosphorothioate backbone; the other, ISIS 10754 (also known as CIBA 1439 or CGP 69845) has a phosphorothioate backbone in the central region (backbone linkages 7–14) and a phosphodiester backbone in the remaining (flanking) regions. These oligonucleotides were tested for their ability to inhibit c-raf mRNA expression in T24 cells. $IC_{50}$s were calculated (oligonucleotide concentration yielding 50% inhibition) and are shown in Table 1 along with Tm data showing affinity of these oligonucleotides for their complement. Because of their extremely low $IC_{50}$s, both ISIS 10755 and ISIS 10754 are preferred.

TABLE 1

Antisense activity in T24 cells and Tm

| ISIS # | Modification | Tm (°C.) | IC$_{50}$ (nM) | SEQ ID NO: |
|---|---|---|---|---|
| 5132 | deoxy/P = S | 62.2 | 125 | 1 |
| 10755 | 2'-O—CH$_2$CH$_2$OCH$_3$/P = S | 76.1 | 20 | 1 |
| 10754 | 2'-O—CH$_2$CH$_2$OCH$_3$/ P = S/P = O | 77.5 | 20 | 1 |

Specificity of ISIS 5132 for raf

Specificity of ISIS 5132 for raf mRNA was demonstrated by a Northern blot assay in which this oligonucleotide was tested for the ability to inhibit Ha-ras mRNA as well as c-raf mRNA in T24 cells. Ha-ras is a cellular oncogene which is implicated in transformation and tumorigenesis. ISIS 5132 was shown to abolish c-raf mRNA almost completely with no effect on Ha-ras mRNA levels.

Chimeric oligonucleotides

Chimeric oligonucleotides having SEQ ID NO: 1 were prepared. These oligonucleotides had central "gap" regions of 6, 8, or 10 deoxynucleotides flanked by two regions of 2'—O—methyl modified nucleotides. Backbones were uniformly phosphorothioate. In Northern blot analysis, all three of these oligonucleotides (ISIS 6720, 6-deoxy gap; ISIS 6717, 8-deoxy gap; ISIS 6729, 10-deoxy gap) showed greater than 70% inhibition of c-raf mRNA expression in T24 cells. The 8-deoxy gap compound (6717) showed greater than 90% inhibition. Oligonucleotides of SEQ ID NO: 1 having an 8-deoxynucleotide gap flanked by either 2'—O—propyl or 2' fluoro modified nucleotides were also found to be active.

Inhibition of cancer cell proliferation

The phosphorothioate oligonucleotide ISIS 5132 (SEQ ID NO: 1) was shown to inhibit T24 bladder cancer cell proliferation. Cells were treated with various concentrations of oligonucleotide in conjunction with lipofectin (cationic lipid which increases uptake of oligonucleotide). A dose-dependent inhibition of cell proliferation was demonstrated, as indicated in Table 2, in which "None" indicates untreated control (no oligonucleotide) and "Control" indicates treatment with negative control oligonucleotide. Results are shown as percent inhibition compared to untreated control.

TABLE 2

Inhibition of T24 Cell Proliferation by ISIS 5132

| Oligo conc. | None | Control | 5132 |
|---|---|---|---|
| 50 nM | 0 | +9% | 23% |
| 100 nM | 0 | +4% | 24% |
| 250 nM | 0 | 10% | 74% |
| 500 nM | 0 | 18% | 82% |

Effect of ISIS 5132 on T24 human bladder carcinoma tumors

Subcutaneous human T24 bladder carcinoma xenografts in nude mice were established and treated with ISIS 5132 and an unrelated control phosphorothioate oligonucleotide administered intraperitoneally three times weekly at a dosage of 25 mg/kg. In this preliminary study, ISIS 5132 inhibited tumor growth after eleven days by 35% compared to controls. Oligonucleotide-treated tumors remained smaller than control tumors throughout the course of the study.

Effect of ISIS 5132 on MDA-MB 231 human breast carcinoma tumors

Subcutaneous human MDA-MB 231 breast carcinoma xenografts in nude mice were established and treated with ISIS 5132 and an unrelated control phosphorothioate oligonucleotide administered intravenously once per day at a dosage of 0.6 mg/kg or 6.0 mg/kg. ISIS 5132 inhibited tumor growth after 27 days (end of study) by approximately 80% compared to controls.

ISIS 5132 was also effective when administered intraperitoneally to MDA-MB 231 xenografts in nude mice. Oligonucleotide was administered once per day at 0.6 mg/kg or 6.0 mg/kg. By day 27 (end of study), tumor volume was inhibited by 57% (0.6 mg/kg dose) or 64% (6.0 mg/kg) compared to control.

Effect of ISIS 5132 on c-raf RNA levels in MDA-MB231 tumors

RNA was isolated from MDA-MD231 tumor xenografts and Northern blots were performed to evaluate oligonucleotide effects on raf RNA levels. ISIS 5132 decreased raf RNA levels after 27 days by 67% when given intravenously and 39% when given intraperitoneally (both at 6 mg/kg).

Effect of ISIS 5132 on Colo 205 human colon carcinoma tumors

Subcutaneous human Colo 205 colon carcinoma xenografts in nude mice were established and treated with ISIS 5132 and an unrelated control phosphorothioate oligonucleotide administered intravenously once per day at a dosage of 6.0 mg/kg. In this study, ISIS 5132 inhibited tumor growth after 25 days by over 40% compared to controls.

Effect of ISIS 5132 on A549 human lung adenocarcinoma tumors

Figure 1A:
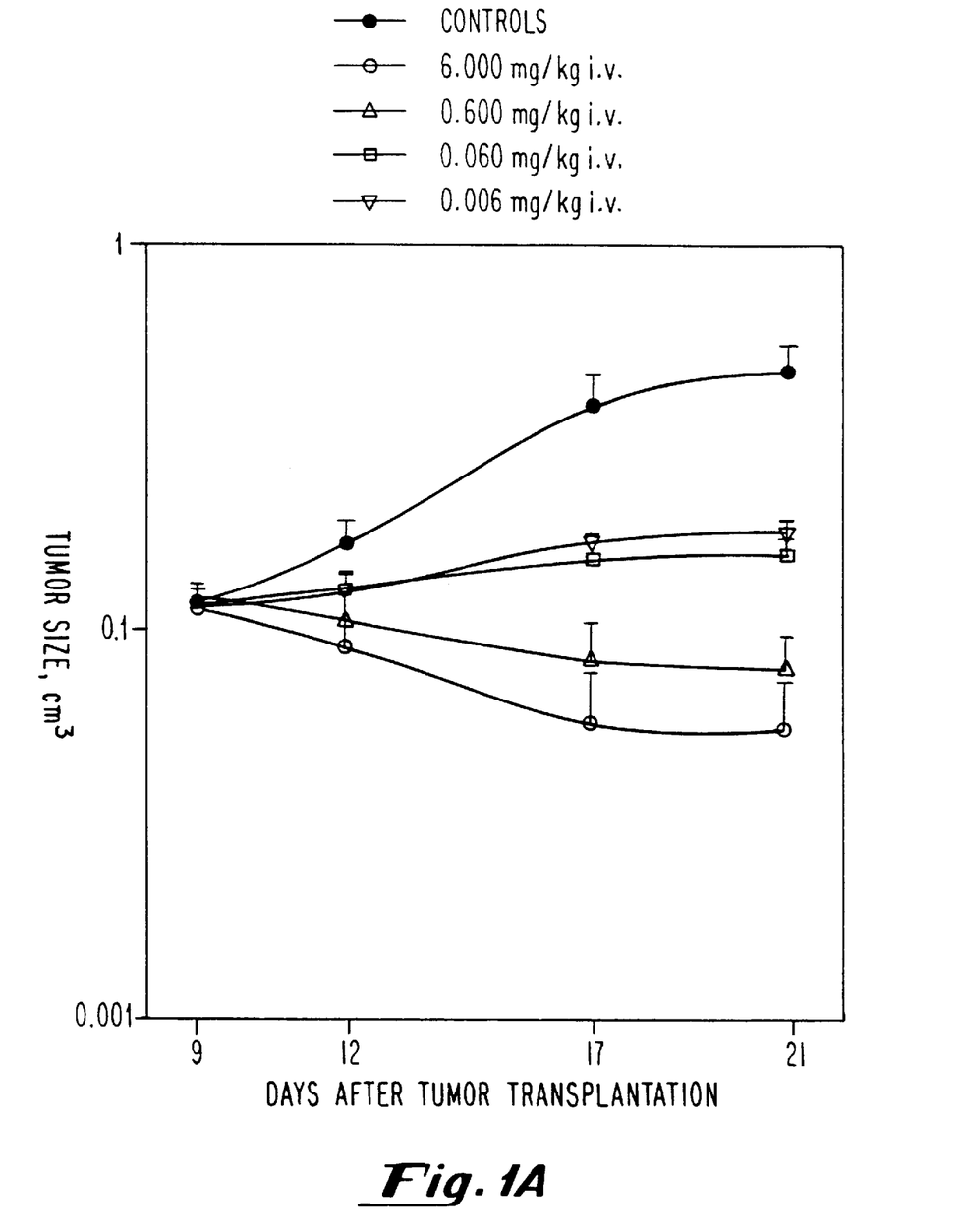
FIGS. 1A and B are line graphs showing the effect of ISIS 5132 (FIG. 1A) and a scrambled control oligonucleotide ISIS 10353 (FIG. 1B) on growth of A549 lung tumor xenografts in nude mice. ISIS 5132 decreased tumor size at all doses (0.006 mg/kg; 0.06 mg/kg; 0.6 mg/kg; and 6.0 mg/kg) in a dose-dependent manner. The scrambled raf oligonucleotide, ISIS 10353, had no effect at any dose (FIG. 1B).
Figure 1B:
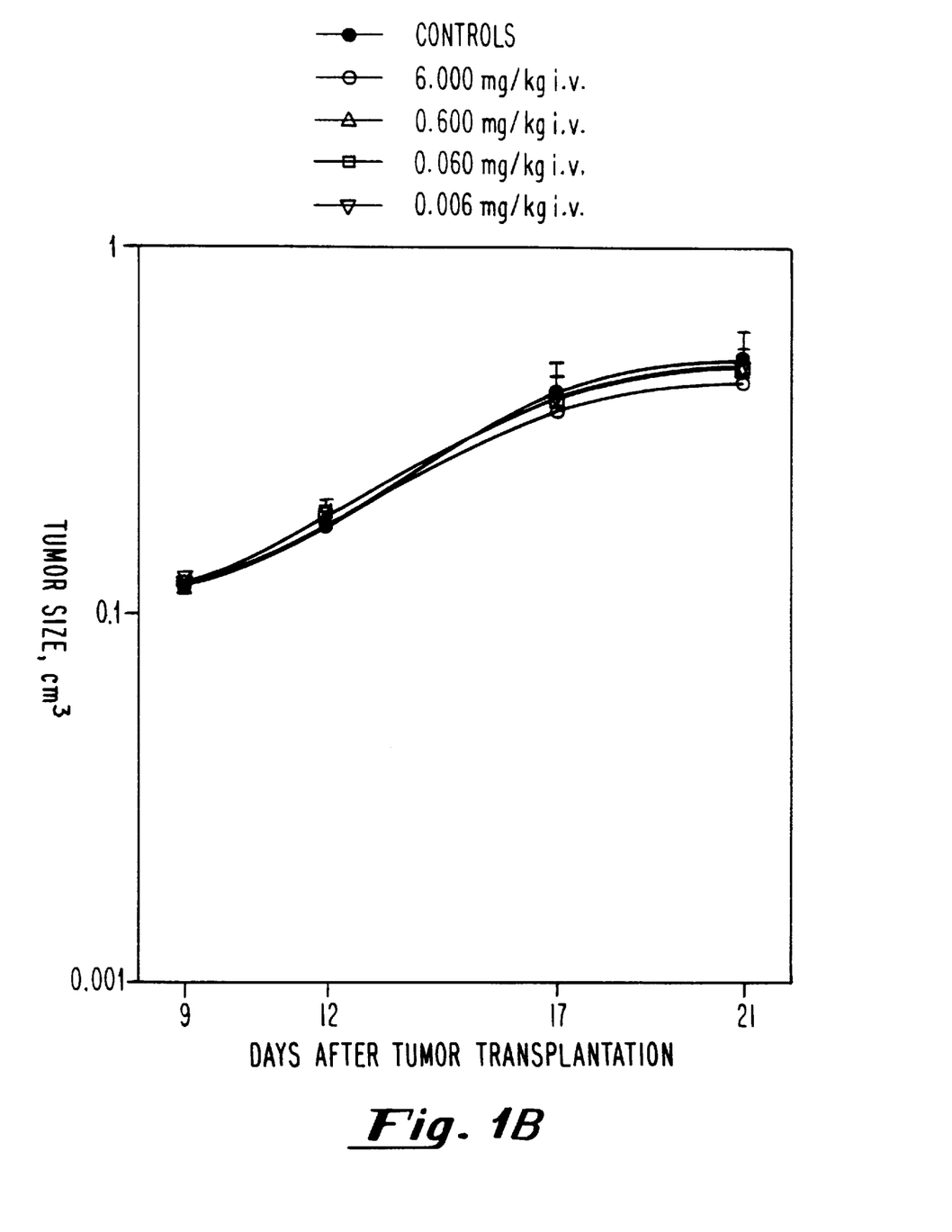

Subcutaneous human A549 lung adenocarcinoma xenografts were established in male Balb/c nude mice and treated with ISIS 5132 and a control oligonucleotide administered daily by intravenous injection at doses ranging from 0.006 to 6.0 mg/kg. ISIS 5132 decreased tumor size at all doses in a dose-dependent manner, as shown in FIG. 1. A scrambled raf oligonucleotide, ISIS 10353, had no effect at any dose.

Effect of ISIS 5132 and CGP 69845 on A549 human lung adenocarcinoma tumors

Figure 2A:
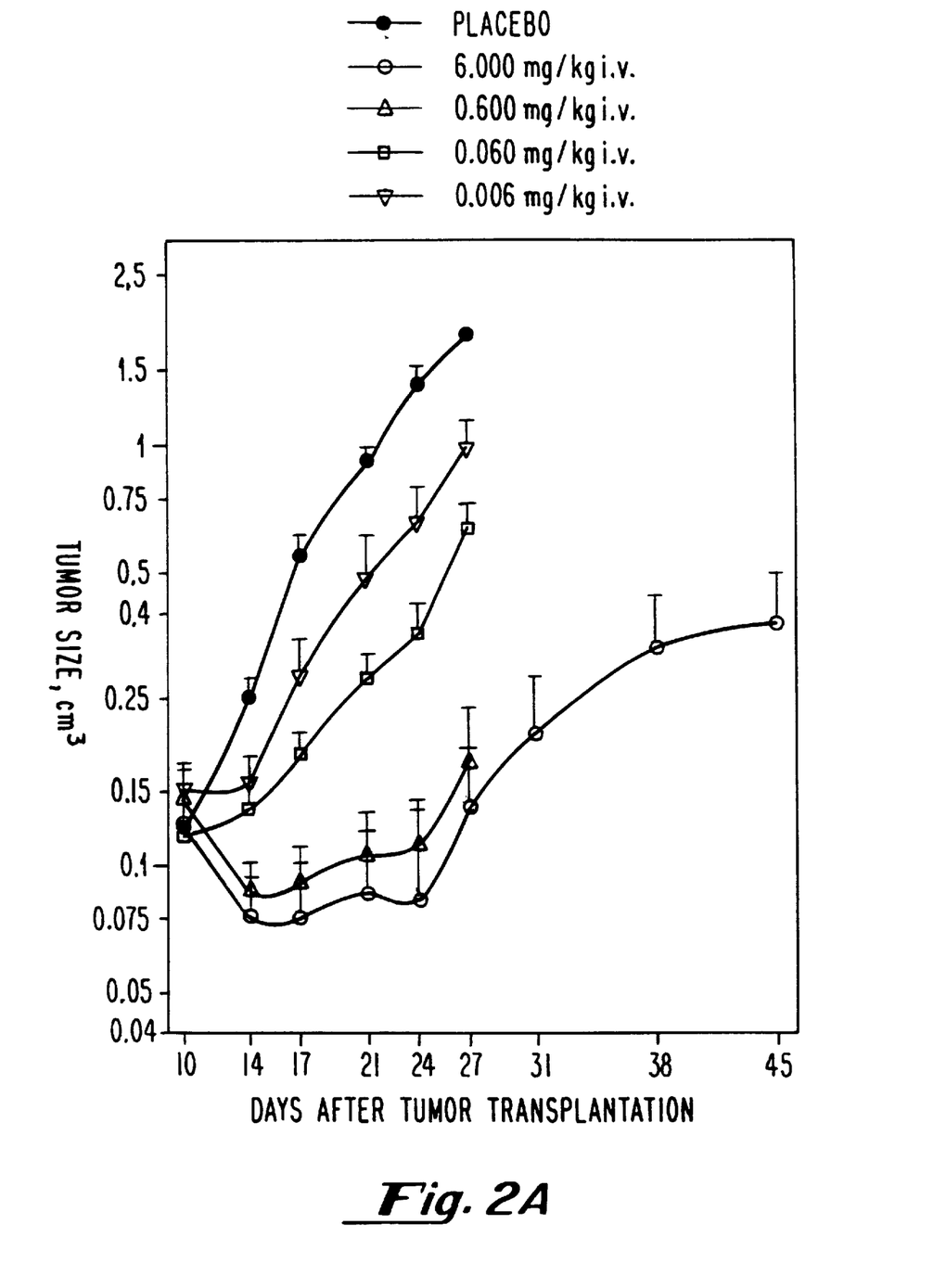
FIGS. 2A and B are line graphs showing the effect of ISIS 5132 and a 2'methoxyethoxy (2'—O—$CH_2CH_2OCH_3$) version of the same sequence, CGP 69845, on growth of A549 lung tumor xenografts in nude mice. ISIS 5132 decreased tumor size at all doses (0.006 mg/kg; 0.06 mg/kg; 0.6 mg/kg; and 6.0 mg/kg) in a dose-dependent manner. The methoxyethoxy (2'—O—$CH_2CH_2OCH_3$) oligonucleotide, CGP 69845 (also known as ISIS 10754), had even greater inhibitory effects than ISIS 5132 at the highest dose.
Figure 2B:
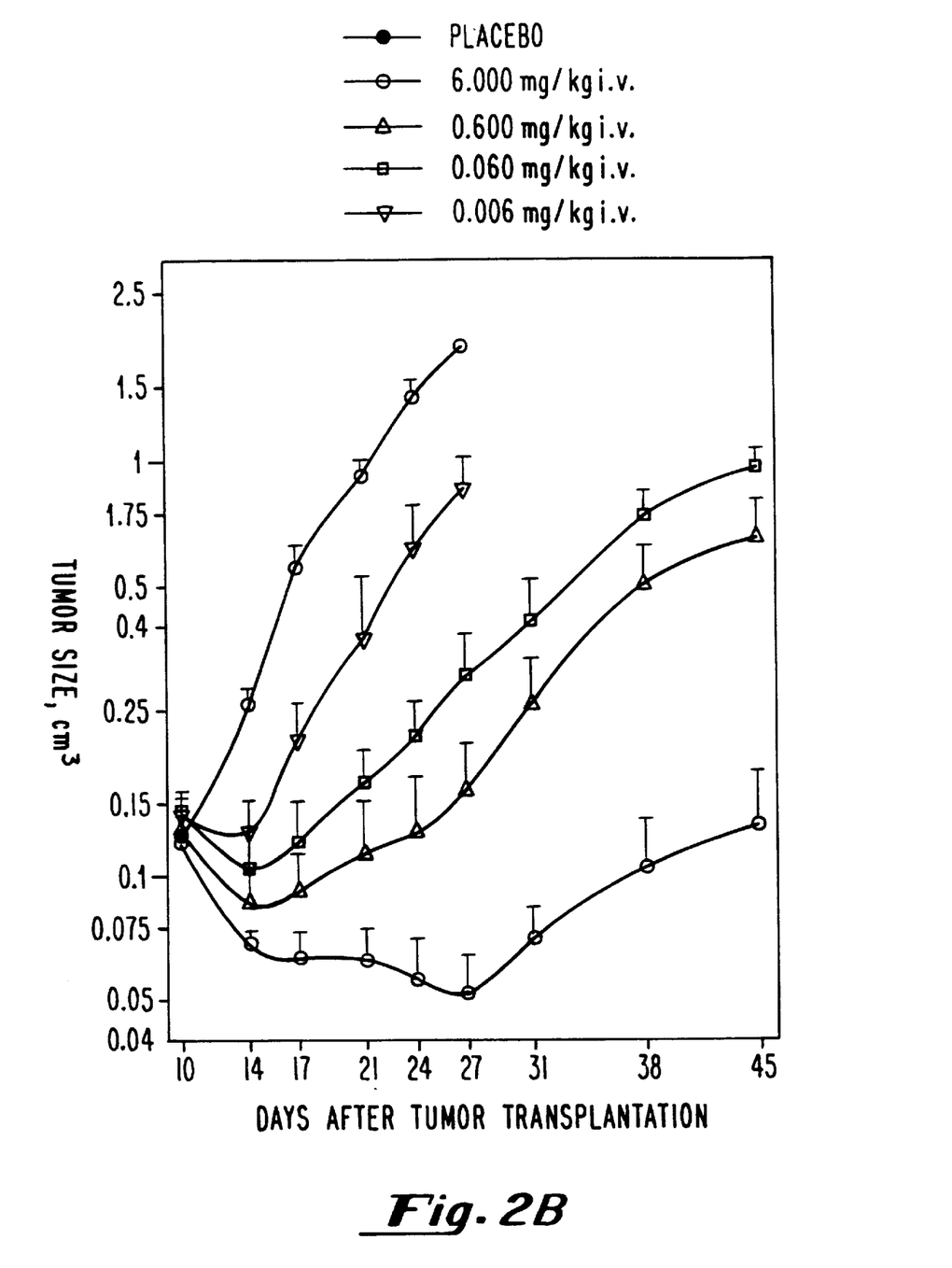

Subcutaneous human A549 lung adenocarcinoma xenografts were established in male Balb/c nude mice and treated with ISIS 5132 (SEQ ID NO: 1) or the methoxyethoxy (2'—O—CH$_2$CH$_2$OCH$_3$) version of SEQ ID NO: 1 (CGP 69845), both administered daily by intravenous injection at doses ranging from 0.006 to 6.0 mg/kg. ISIS 5132 decreased tumor size at all doses in a dose-dependent manner, as shown in FIG. 2. The methoxyethoxy (2'—O—CH$_2$CH$_2$OCH$_3$) oligonucleotide, CGP 69845, had similar effects to ISIS 5132 at the lower doses and even greater inhibitory effects than ISIS 5132 at 6.0 mg/kg.

Effect of ISIS 5132 on c-raf RNA levels in A549 tumor cells

RNA was isolated from A549 tumor xenografts and Northern blots were performed to evaluate oligonucleotide effects on raf RNA levels. ISIS 5132 progressively decreased raf RNA levels beginning 8 hours after start of oligo treatment. When the experiment was terminated at day 13, RNA levels were still declining and had reached levels approximately 15% of control.

Identification of oligonucleotides targeted to rat and mouse c-raf

Many conditions which are believed to be mediated by raf kinase are not amenable to study in humans. For example, tissue graft rejection is a condition which is likely to be ameliorated by interference with raf expression; but, clearly, this must be evaluated in animals rather than human transplant patients. Another such example is restenosis. These conditions can be tested in animal models, however, such as the rat and mouse models used here. These data provide added evidence of the therapeutic utility of antisense oligonucleotides targeted to c-raf.

Oligonucleotide sequences for inhibiting c-raf expression in rat and mouse cells were identified. Rat and mouse c-raf genes have regions of high homology; a series of oligonucleotides which target both rat and mouse c-raf MRNA sequence were designed and synthesized, using information gained from evaluation of oligonucleotides targeted to human c-raf. These oligonucleotides were screened for activity in mouse bEND cells and rat A-10 cells using Northern blot assays. Two oligonucleotides, ISIS 11061 and ISIS 10707, were found to inhibit c-raf RNA levels by greater than 90% in mouse bEND cells at a dose of 400 nM. These two oligonucleotides inhibited raf RNA levels virtually entirely in rat A-10 cells at a concentration of 200 nM. The IC50 for ISIS 10707 was found to be 170 nM in mouse bEND cells and 85 nM in rat A-10 cells. The IC50 for ISIS 11061 was determined to be 85 nM in mouse bEND cells and 30 nM in rat A-10 cells.

Effect of ISIS-11061 on endogenous c-raf MRNA expression in ice

Mice were injected intraperitoneally with ISIS 11061 (50 mg/kg) or control oligonucleotide or saline control once daily for three days. Animals were sacrificed and organs were analyzed for c-raf mRNA expression by Northern blot analysis. ISIS 11061 was found to decrease levels of c-raf mRNA in liver by approximately 70%. Control oligonucleotides had no effects on c-raf expression. The effect of ISIS 11061 was specific for c-raf; A-raf and G3PDH RNA levels were unaffected by oligonucleotide treatment.

Antisense oligonucleotide to c-raf increases survival in murine heart allograft model To determine the therapeutic effects of the c-raf antisense oligonucleotide ISIS 11061 in preventing allograft rejection, this oligonucleotide was tested for activity in a murine vascularized heterotopic heart transplant model. Hearts from C57BI10 mice were transplanted into the abdominal cavity of C3H mice as primary vascularized grafts essentially as described by Isobe et al., Circulation 1991, 84, 1246–1255. Oligonucleotides were administered by continuous intravenous administration via a 7-day Alzet pump. The mean allograft survival time for untreated mice was 7.83±0.75 days(7, 7, 8, 8, 8, 9 days). Allografts in mice treated for 7 days with 20 mg/kg or 40 mg/kg ISIS 11061 all survived at least 11 days (11, 11, 12 days for 20 mg/kg dose and >11, >11, >11 days for the 40 mg/kg dose).

In a pilot study conducted in rats, hearts from Lewis rats were transplanted into the abdominal cavity of ACI rats. Rats were dosed with ISIS 11061 at 20 mg/kg for 7 days via Alzet pump. The mean allograft survival time for untreated rats was 8.86±0.69 days (8, 8, 9, 9, 9, 9, 10 days). In rats treated with oligonucleotide, the allograft survival time was 15.3±1.15 days (14, 16, 16 days).

Effects of antisense oligonucleotide targeted to c-raf on smooth muscle cell proliferation Smooth muscle cell proliferation is a cause of blood vessel stenosis, for example in atherosclerosis and restenosis after angioplasty. Experiments were performed to determine the effect of ISIS 11061 on proliferation of A-10 rat smooth muscle cells. Cells in culture were grown with and without ISIS 11061 (plus lipofectin) and cell proliferation was measured 24 and 48 hours after stimulation with fetal calf serum. ISIS 11061 (500 nM) was found to inhibit serum-stimulated cell growth in a dosedependent manner with a maximal inhibition of 46% and 75% at 24 hours and 48 hours, respectively. An IC50 value of 200 nM was obtained for this compound. An unrelated control oligonucleotide had no effect at doses up to 500 nM.

Effects of antisense oligonucleotides targeted to c-raf on restenosis in rats

A rat carotid artery injury model of angioplasty restenosis has been developed and has been used to evaluate the effects on restenosis of antisense oligonucleotides targeted to the c-myc oncogene. Bennett et al., J. Clin. Invest. 1994, 93, 820–828. This model will be used to evaluate the effects of antisense oligonucleotides targeted to rat c-raf, particularly ISIS 11061, on restenosis. Following carotid artery injury with a balloon catheter, oligonucleotides are administered either by intravenous injection, continuous intravenous administration via Alzet pump, or direct administration to the carotid artery in a pluronic gel matrix as described by Bennett et al. After recovery, rats are sacrificed, carotid arteries are examined by microscopy and effects of treatment on luminal cross-sections are determined.

The invention is further illustrated by the following examples which are illustrations only and are not intended to limit the present invention to specific embodiments.

EXAMPLES

Example 1 Synthesis and characterization of oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites were purchased from Applied Biosystems (Foster City, Calif.). For phosphorothioate oligonucleotides, the standard oxidation bottle was replaced by a 0.2 M solution of H-1,2-benzodithiole-3-one 1,1-dioxide in acetonitrile for the stepwise thiation of the phosphite linkages. The thiation cycle wait step was increased to 68 seconds and was followed by the capping step. 2'—O—methyl phosphorothioate oligonucleotides were synthesized using 2'—O—methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'—O—propyl oligonucleotides were prepared by a slight modification of this procedure.

2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

The methoxyethoxy (2'—O—$CH_2CH_2OCH_3$) oligonucleotides were synthesized according to the method of Martin, Helv. Chim. Acta 1995, 78,486–504.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

Example 2 Northern blot analysis of inhibition of c-raf mRNA expression

The human urinary bladder cancer cell line T24 was obtained from the American Type Culture Collection (Rockville Md.). Cells were grown in McCoy's SA medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 Al DOTMA. Oligonucleotide with lipofectin was then added to the desired concentration. After 4 hours of treatment, the medium was replaced with McCoy's medium. Cells were harvested 24 to 72 hours after oligonucleotide treatment and RNA was isolated using a standard CsCl purification method. Kingston, R. E., in Current Protocols in Molecular Biology, (F. M. Ausubel, R. Brent, R. E. Kingston, D. D. Moore, J. A. Smith, J. G. Seidman and K. Strahl, eds.), John Wiley and Sons, N.Y. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to random-primed $^{32}$P-labeled c-raf cDNA probe (obtained from ATCC) or G3PDH probe as a control. RNA was quantitated using a Phosphorimager (Molecular Dynamics, Sunnyvale, Calif.).

Example 3 Specific inhibition of c-raf kinase protein expression in T24 cells

T24 cells were treated with oligonucleotide (200 nM) and lipofectin at T=0 and T=24 hours. Protein extracts were prepared at T=48 hours, electrophoresed on acrylamide gels and analyzed by Western blot using polyclonal antibodies against c-raf (UBI, Lake Placid, N.Y.) or A-raf (Transduction Laboratories, Knoxville, Tenn.). Radiolabeled secondary antibodies were used and raf protein was quantitated using a Phosphorimager (Molecular Dynamics, Sunnyvale Calif.).

Example 4 Antisense inhibition of cell proliferation

T24 cells were treated on day 0 for two hours with various concentrations of oligonucleotide and lipofectin (50 nM oligonucleotide in the presence of 2 μg/ml lipofectin; 100 nM oligonucleotide and 2 μg/ml lipofectin; 250 nM oligonucleotide and 6 μg/ml lipofectin or 500 nM oligonucleotide and 10 μg/ml lipofectin). On day 1, cells were treated for a second time at desired oligonucleotide concentration for two hours. On day 2, cells were counted.

Example 5 Effect of ISIS 5132 on T24 human bladder carcinoma tumor xenografts in nude mice $5 \times 10^6$ T24 cells were implanted subcutaneously in the right inner thigh of nude mice. Oligonucleotides (ISIS 5132 and an unrelated control phosphorothioate oligonucleotide suspended in saline) were administered three times weekly beginning on day 4 after tumor cell inoculation. A saline-only control was also given. Oligonucleotides were given by intraperitoneal injection. Oligonucleotide dosage was 25 mg/kg. Tumor size was measured and tumor volume was calculated on the eleventh, fifteenth and eighteenth treatment days.

Example 6 Effect of ISIS 5132 on MDA-MB 231 human breast carcinoma tumor xenografts in nude mice $5 \times 10^6$ MDA-MB 231 cells were implanted subcutaneously in the right inner thigh of nude mice. Oligonucleotides (ISIS 5132 and an unrelated control phosphorothioate oligonucleotide suspended in saline) were administered once daily beginning on day 10 after tumor cell inoculation. A saline-only control was also given. oligonucleotideswere-givenbyintravenousinjection at a dosage of 0.6 mg/kg or 6.0 mg/kg. Tumor size was measured and tumor volume was calculated on days 10, 13, 16, 20, 23 and 27 following tumor cell inoculation.

For intraperitoneal oligonucleotide administration, oligonucleotides were administered once daily beginning on day 10 after tumor cell inoculation. A saline-only control was also given. Oligonucleotides were given by intraperitoneal injection at a dosage of 0.6 mg/kg or 6.0 mg/kg. Tumor size was measured and tumor volume was calculated on days 10, 13, 16, 20, 23 and 27 following tumor cell inoculation.

Example 7 Effect of ISIS 5132 on Colo 205 human colon carcinoma tumor xenografts in nude mice $5 \times 10^5$ Colo 205 cells were implanted subcutaneously in the right inner thigh of nude mice. oligonucleotides (ISIS 5132 and an unrelated control phosphorothioate oligonucleotide suspended in saline) were administered once per day beginning on day 5 after tumor cell inoculation. A saline-only control was also given. Oligonucleotides were given by intravenous injection. Oligonucleotide dosage was 6 mg/kg. Tumor size was measured and tumor volume was calculated on days 5, 8, 11, 14, 18, 22 and 25 after tumor inoculation.

Example 8 Diagnostic assay for raf-associated tumors using xenografts in nude mice Tumors arising from raf expression are diagnosed and distinguished from other tumors using this assay. A biopsy sample of the tumor is treated, e.g., with collagenase or trypsin or other standard methods, to dissociate the tumor mass. $5 \times 10^6$ tumor cells are implanted subcutaneously in the inner thighs of two or more nude mice. Antisense oligonucleotide (e.g., ISIS 5132) suspended in saline is administered to one or more mice by intraperitoneal injection three times weekly beginning on day 4 after tumor cell inoculation. Saline only is given to a control mouse. Oligonucleotide dosage is 25 mg/kg. Tumor size is measured and tumor volume is calculated on the eleventh treatment day. Tumor volume of the oligonucleotide-treated mice is compared to that of the control mouse. The volume of raf-associated tumors in the treated mice are measurably smaller than tumors in the control mouse. Tumors arising from causes other than raf expression are not expected to respond to the oligonucleotides targeted to raf and, therefore, the tumor volumes of oligonucleotide- treated and control mice are equivalent.

Example 9 Detection of raf expression

Oligonucleotides are radiolabeled after synthesis by $^{32}$P labeling at the 5' end with polynucleotide kinase. Sambrook et al., Molecular Cloning. A Laboratory Manual, Cold Spring Harbor Laboratory Press, 1989, Volume 2, pg. 11.31–11.32. Radiolabeled oligonucleotides are contacted with tissue or cell samples suspected of raf expression, such as tumor biopsy samples or skin samples where psoriasis is suspected, under conditions in which specific hybridization can occur, and the sample is washed to remove unbound oligonucleotide. Radioactivity remaining in the sample indicates bound oligonucleotide and is quantitated using a scintillation counter or other routine means. Radiolabeled oligonucleotides of the invention are also used in autoradiography. Tissue sections are treated with radiolabeled oligonucleotide and washed as described above, then exposed to photographic emulsion according to standard autoradiography procedures. The emulsion, when developed, yields an image of silver grains over the regions expressing raf. The extent of raf expression is determined by quantitation of the silver grains.

Analogous assays for fluorescent detection of raf expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of oligonucleotide and biological sample is carried out as described for radiolabeled oligonucleotides except that instead of a scintillation counter, a fluorimeter or fluorescence microscope is used to detect the fluorescence which indicates raf expression.

Example 10 A549 xenografts $5 \times 10^6$ A549 cells were implanted subcutaneously in the inner thigh of nude mice. Oligonucleotides (ISIS 5132 and CGP 69845, also known as ISIS 10754) suspended in saline were administered once daily by intravenous injection at doses ranging from 0.006 to 6.0 mg/kg. Resulting tumors were measured on days 9, 12, 17 and 21 and tumor volumes were calculated.

Example 11 Effect of oligonucleotide on endogenous c-raf expression

Mice were treated by intraperitoneal injection at an oligonucleotide dose of 50 mg/kg on days 1, 2 and 3. On day 4, animals were sacrificed and organs removed for c-raf mRNA assay by Northern blot analysis. Four groups of animals were employed: 1) no oligonucleotide treatment (saline); 2) negative control oligonucleotide ISIS 1082 (targeted to herpes simplex virus; 3) negative control oligonucleotide 4189 (targeted to mouse protein kinase C-a; 4) ISIS 11061 targeted to rodent c-raf.

Example 12 Cardiac allograft rejection model

Hearts were transplanted into the abdominal cavity of rats or mice (of a different strain from the donor) as primary vascularized grafts essentially as described by Isobe et al., Circulation 1991, 84, 1246–1255. Oligonucleotides were administered by continuous intravenous administration via a 7-day Alzet pump. Cardiac allograft survival was monitored by listening for the presence of a second heartbeat in the abdominal cavity.

Example 13 Proliferation assay using rat A-10 smooth muscle cells

A10 cells were plated into 96-well plates in Dulbecco's modified Eagle medium (DMEM) +10% fetal calf serum and allowed to attach for 24 hours. Cells were made quiescent by the addition of DMEM +0.2% dialyzed fetal calf serum for an additional 24 hours. During the last 4 hours of quiescence, cells were treated with ISIS 11061 +lipofectin (Gibco-BRL, Bethesda Md.) in serum-free medium. Medium was then removed, replaced with fresh medium and the cells were stimulated with 10% fetal calf serum. The plates were the placed into the incubator and cell growth was evaluated by MTS conversion to formozan (Promega cell proliferation kit) at 24 and 48 hours after serum stimulation. A control oligonucleotide, ISIS 1082 (an unrelated oligonucleotide targeted to herpes simplex virus), was also tested.

Example 14 Rat carotid artery restenosis model

This model has been described by Bennett et al., J. Clin. Invest. 1994, 93, 820–828. Intimal hyperplasia is induced by balloon catheter dilatation of the carotid artery of the rat. Rats are anesthetized and common carotid artery injury is induced by passage of a balloon embolectomy catheter distended with 20 ml of saline. Oligonucleotides are applied to the adventitial surface of the arterial wall in a pluronic gel solution. Oligonucleotides are dissolved in a 0.25% pluronic gel solution at 4° C. (F127, BASF Corp.) at the desired dose. 100 µl of the gel solution is applied to the distal third of the common carotid artery immediately after injury. Control rats are treated similarly with gel containing control oligonucleotide or no oligonucleotide. The neck wounds are closed and the animals allowed to recover. 14 days later, rats are sacrificed, exsanguinated and the carotid arteries fixed in situ by perfusion with paraformaldehyde and glutaraldehyde, excised and processed for microscopy. Cross-sections of the arteries are calculated.

In an alternative to the pluronic gel administration procedure, rats are treated by intravenous injection or continuous intravenous infusion (via Alzet pump) of oligonucleotide.

What is claimed is:

1. A method of treating an abnormal proliferative condition comprising contacting a human, or cells, tissues or a bodily fluid of said human, suspected of having an abnormal proliferative condition with an oligonucleotide consisting of SEQ ID NO: 1 and at least one 2'—O—$CH_2CH_2OCH_3$ modification.

2. The method of claim wherein the condition is a hyperproliferative disorder.

3. The method of claim 2 wherein the hyperproliferative disorder is cancer.

4. A method of increasing allograft survival time in a human wherein rejection of said allograft is mediated by raf kinase, said method comprising inhibiting human raf expression by administering to said human an oligonucleotide consisting of the sequence of SEQ.ID. NO: 1, wherein said oligonucleotide further comprises at least one 2'—O—$CH_2CH_2$—O—$CH_3$ modification.

* * * * *

UNITED STATES PATENT AND TRADEMARK OFFICE
CERTIFICATE OF CORRECTION

PATENT NO. : 5,919,773
DATED : July 6, 1999
INVENTOR(S) : Monia et al.

It is certified that error appears in the above-indentified patent and that said Letters Patent is hereby corrected as shown below:

At col 1, line 56, please delete "influenzavirus" and insert therefor --influenza virus--.

At col 2, line 20, please delete "Wo" and insert therefor --WO--.

At col 2, line 32, please delete "Wo" and insert therefor --WO--.

At col 4, line 26, please delete "sequence hose" and insert therefor --sequence whose--.

At col 5, line 7, please delete "MRNA" and insert therefor --mRNA--.

At col 5, line 54, please delete "RNAse" and insert therefor --RNase--.

At col 5, line 66, please delete "RNAse" and insert therefor --RNase--.

UNITED STATES PATENT AND TRADEMARK OFFICE
CERTIFICATE OF CORRECTION

PATENT NO. : 5,919,773
DATED : July 6, 1999
INVENTOR(S) : Monia et al.

It is certified that error appears in the above-indentified patent and that said Letters Patent is hereby corrected as shown below:

At col 8, line 3, please delete "$^{32}$p" and insert therefor --$^{32}$P--.

At col 11, line 9, please delete "MRNA" and insert therefor --mRNA--.

At col 11, line 67, please delete "dosedependent" and insert therefor --dose-dependent--.

At col 13, line 5, please delete "SA medium" and insert therefor --5A medium--.

At col 13, line 12, please delete "2.5 Al" and insert therefor --2.5 µl--.

UNITED STATES PATENT AND TRADEMARK OFFICE
CERTIFICATE OF CORRECTION

PATENT NO. : 5,919,773
DATED : July 6, 1999
INVENTOR(S) : Monia et al.

It is certified that error appears in the above-indentified patent and that said Letters Patent is hereby corrected as shown below:

At col 18, line 1, please delete "SEQ.ID.NO." and insert therefor --SEQ ID NO--.

At col 14, lines 3-4, please delete "oligonucleotidesweeregivenbyintravenousinjection" and insert therefor --oligonucleotides were given by intravenous injection--.

At col 15, line 32, please delete "C-a" and insert therefor --C-$\alpha$--.

At col 16, line 64, please delete "SEO ID NO:" and insert therefor --SEQ ID NO:--.

UNITED STATES PATENT AND TRADEMARK OFFICE
CERTIFICATE OF CORRECTION

PATENT NO. : 5,919,773
DATED : July 6, 1999
INVENTOR(S) : Monia et. al.

It is certified that error appears in the above-identified patent and that said Letters Patent is hereby corrected as shown below:

At col 16, line 66, please delete "method of claim wherein" and insert therefor --method of claim 1 wherein--.

Signed and Sealed this

Twenty-fifth Day of July, 2000

Attest:

Q. TODD DICKINSON

Attesting Officer

Director of Patents and Trademarks